United States Patent [19]

Bundy

[11] 4,098,805
[45] Jul. 4, 1978

[54] 9-DEOXY-9-METHYLENE-PGF-TYPE AMIDES

[75] Inventor: Gordon L. Bundy, Portage, Mich.

[73] Assignee: The Upjohn Company, Kalamazoo, Mich.

[21] Appl. No.: 786,250

[22] Filed: Apr. 11, 1977

[51] Int. Cl.$^2$ ............... C07C 103/19; C07C 103/26; A61K 31/16; A61K 31/165

[52] U.S. Cl. ............... 260/404; 260/239 BF; 260/290 H; 260/293.73; 260/326.4; 260/556 A; 260/556 AC; 260/557 R; 260/559 R; 542/426; 542/429; 560/61; 560/62; 560/219; 560/220; 424/320; 424/324; 544/172; 544/174; 544/173; 544/391

[58] Field of Search ............... 260/404, 557 R, 559 R, 260/514 D

[56] References Cited

U.S. PATENT DOCUMENTS

| | | |
|---|---|---|
| 3,890,372 | 6/1975 | Morozowich ............... 560/121 |
| 3,927,197 | 12/1975 | Monkhouse ............... 260/557 R X |
| 3,954,741 | 5/1976 | Schaaf et al. ............... 260/557 R X |
| 3,981,868 | 9/1976 | Bernady et al. ............... 542/429 |
| 4,060,534 | 11/1977 | Bundy ............... 260/408 |

Primary Examiner—Daniel E. Wyman
Assistant Examiner—Thomas A. Waltz
Attorney, Agent, or Firm—Robert A. Armitage

[57] ABSTRACT

The present invention relates in part to novel amido, cycloamido, carbonylamido and sulfonylamido derivatives and p-substituted phenyl esters of 9-deoxy-9-methylene-PGF-type compounds. These novel amides produce surprisingly prolonged oral activity as pharmacological agents, as compared to the previously known 9-deoxy-9-methylene-PGF-type compounds.

Further, the novel p-substituted phenyl esters provide more stable pharmaceutical formulations as compared to known 9-deoxy-9-methylene-PGF-type esters.

Additionally, a novel series of 16-phenyl-9-deoxy-9-methylene-PGF-type compounds in free acid, ester, C-1 alcohol, and C-1 amine form is provided. Such compounds exhibit characteristic prostaglandin-type pharmacological actions.

38 Claims, No Drawings

9-DEOXY-9-METHYLENE-PGF-TYPE AMIDES

BACKGROUND OF THE INVENTION

The present invention relates to novel amido, cycloamido, carbonylamido, sulfonylamido, p-substituted phenoxy derivatives of 9-deoxy-9-methylene-PGF-type acids. These 9-deoxy-9-methylene-PG-type acids are known to be structural and pharmacological analogs of the prostaglandins. Further, novel 16-phenyl-9-deoxy-9-methylene-PGF-type compounds are described herein as such.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions.

Likewise, 9-deoxy-9-methylene-PGF-type compounds represent pharmacological agents exhibiting improved utility as compared to the known prostaglandins. Most especially, these 9-deoxy-9-methylene-PGF-type compounds are employed as regulators of mammalian fertility and procreation (being estrus or menstrual cycle regulators, labor inducers, abortafacients) and anti-asthma and antithrombotic agents.

The preparation of 9-deoxy-9-methylene-PGF-type compounds is described in U.S. application Ser. No. 682,848, filed May 4, 1976, now U.S. Pat. No. 4,060,534, the disclosure of which is incorporated by reference herein. Particularly, there are described therein the preparation of all but the novel 16-phenyl-9-deoxy-9-methylene-PGF-type compounds whose preparation is described hereinafter.

In addition to the above art, which is descriptive of methods for preparing acids or ester derivatives, as well as C-1 alcohols or C-1 amines, of certain prostaglandin type compounds, the preparation of prostaglandin-type amides is likewise accomplished by known methods. For example, see U.S. Pat. No. 3,981,868, issued Sept. 21, 1976, for description of the preparation of certain amido and cycloamido derivatives of 11-deoxy-PG-type compounds.

Further, U.S. Pat. No. 3,954,741, issued May 4, 1976, describes the preparation of certain carbonylamido and sulfonylamido derivatives of various prostaglandin analogs.

Finally, see U.S. Pat. No. 3,890,372, issued June 17, 1975 for a description of the preparation of various p-substituted phenoxy derivatives (i.e. p-substituted phenyl esters) of various prostaglandins.

SUMMARY OF THE INVENTION

The present invention comprises the surprising and unexpected discovery that certain novel amido, cycloamido, carbonylamido, and sulfonylamido derivatives of 9-deoxy-9-methylene-PGF-type compounds exhibit prolonged oral activity as pharmacological agents. Particularly, the present invention comprises the surprising and unexpected discovery that such nitrogen-containing derivatives of 9-deoxy-9-methylene-PGF-type compounds are surprisingly and unexpectedly more useful than the corresponding known free acid and ester derivatives in fertility and procreation control, and antiasthma, and antithrombotic therapy.

Moreover the present invention provides novel p-substituted phenoxy derivatives exhibiting improved physical properties (e.g., stability and in many cases crystallinity). Finally, novel 16-phenyl-9-deoxy-9-methylene-PGF-type compounds are provided.

In particular, the present invention comprises:

(1) a prostaglandin analog of the formula

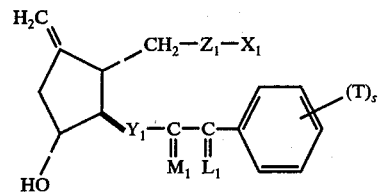

wherein
$Y_1$ is trans—CH=CH—, —C≡C—, or —CH$_2$CH$_2$—;
wherein
$M_1$ is

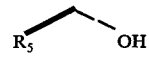

or

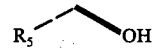

wherein
$R_5$ is hydrogen or methyl;
wherein
$L_1$ is

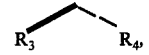

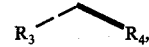

or a mixture of

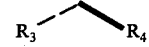

and

wherein
$R_3$ and $R_4$ are hydrogen, methyl, or fluoro, being the same or different, with the proviso that one of $R_3$ and $R_4$ is fluoro only when the other is hydrogen or fluoro;
wherein
$Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

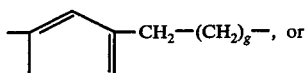 (9)

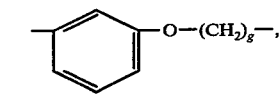 (10)

wherein
g is one, 2, or 3;
wherein
T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein
$X_1$ is
 (1) —COOR$_1$
wherein
$R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
 (2) —CH$_2$OH, or
 (3) —CH$_2$NL$_2$L$_3$
wherein
$L_2$ and $L_3$ are hydrogen, alkyl of one to 4 carbon atoms, inclusive, or —COOR$_1$, wherein $R_1$ is as defined above; and the 1,11- or 1,15-lactones thereof; or
 (2) a prostaglandin analog of the formula

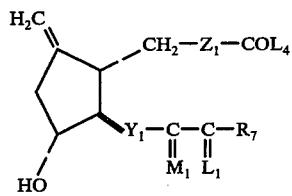 II wherein
$Z_1$, $Y_1$, $M_1$, and $L_1$ are as defined above;
wherein
$R_7$ is
 (1) —(CH$_2$)$_m$—CH$_3$,

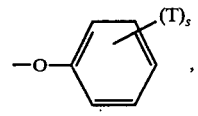 (2)

or

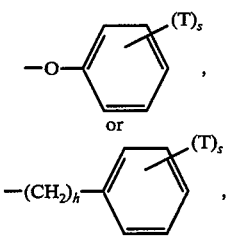 (3)

wherein
m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same of different, with the proviso that not more than two T's are other than alkyl, with the further proviso that $R_7$ is

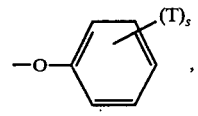, wherein
T and s are as defined above, only when $R_3$ and $R_4$ are hydrogen or methyl, being the same or different; and
wherein
$L_4$ is
 (1) amido of the formula —NR$_{21}$R$_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;
 (2) cycloamido selected from the group consisting of

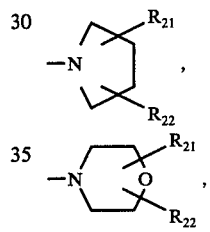 , 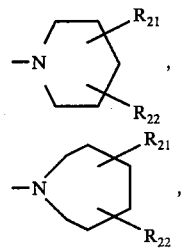 ,

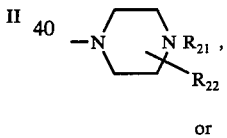 , 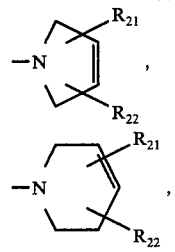 , or wherein
$R_{21}$ and $R_{22}$ are as defined above;
 (3) carbonylamido of the formula —NR$_{23}$COR$_{21}$, wherein $R_{23}$ is hydrogen or alkyl of one to 4 carbon atoms and $R_{21}$ is as defined above;
 (4) sulphonylamido of the formula —NR$_{23}$SO$_2$R$_{21}$, wherein $R_{21}$ and $R_{23}$ are as defined above; or
 (5) p-substituted phenoxy selected from the group consisting of

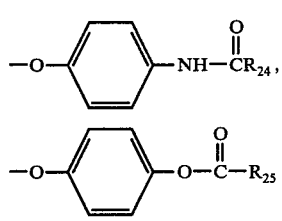

-continued

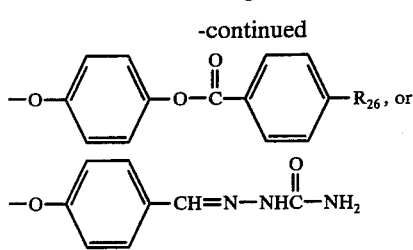

wherein
R$_{24}$ is methyl, phenyl, acetamidophenyl, benzamidophenyl, or —NH$_2$; R$_{25}$ is methyl, phenyl, —NH$_2$, or methoxy; and R$_{26}$ is hydrogen or acetamido.

For convenience, the novel prostaglandin analogs described above will be referred to by the trivial, art-recognized system of nomenclature described by N. A. Nelson, Journal of Medicinal Chemistry, 17, 911 (1974). Accordingly, 9-deoxy-9-methylene-16-phenyl-17,18,19,20-tetranor-PGF$_2$, methyl ester is represented by formula I, above, when X$_1$ is —COOCH$_3$, Z$_1$ is cis—CH=CH—(CH$_2$)$_5$—, Y$_1$ is trans—CH=CH—, R$_3$, R$_4$, and R$_5$ are all hydrogen and the hydroxy of the M$_1$ moiety is in the alpha configuration, and s is zero. The C-15 epimer of the compound named above (15-epi-9-deoxy-9-methylene-16-phenyl-17,18,19,20-tetranor-PGF$_2$, methyl ester) is represented above when the hydroxy of the M$_1$ moiety is in the beta configuration. See particularly U.S. Ser. No. 682,848, now U.S. Pat. No. 4,060,534, for description of the various conventions with respect to the stereochemistry at C-15 as employed herein.

In formulas I and II above, as well as in formulas hereinafter, broken line attachments to the cyclopentane ring indicate substituents in "alpha" ($\alpha$) configuration i.e., below the plane of the cyclopentane ring. Heavy solid line attachments to the cyclopentane ring indicate substituents in "beta" ($\beta$) configuration, i.e., above the plane of the cyclopentane ring. The use of wavy lines (~) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). See, also Nature 212, 38 (1966) for discussion of the stereochemistry of the prostaglandins. As used herein, expressions such as C-2, C-15, and the like, refer to the carbon atom in the prostaglandin analog which is in the position corresponding to the position of the same number in prostanoic acid.

Molecules of the known prostaglandins and asymmetric PG analogs each have several centers of asymmetry, and can exist in racemic (optically inactive) form and in either of the two enantiomeric (optically active) forms, i.e. the dextrorotatory and levorotatory forms. As drawn, the above formulas represent the particular optically active form of the prostaglandin analogs as described herein which correspond to those stereoisomers of known prostaglandins as obtained from mammalian tissues, for example, sheep vesicular glands, swine lung, or human seminal plasma, In particular, refer to the stereoconfiguration at C-8 (alpha), C-11 (alpha), and C-12 (beta) of endogenously-produced PGF$_2\alpha$. The mirror image of the above formulas represent the other enantiomer of these prostaglandin analogs. The racemic forms of such prostaglandin analogs contain equal numbers of both enantiomeric molecules, and the above formulas and their respective mirror images are needed to represent correctly the corresponding racemic prostaglandin analogs.

For convenience hereinafter, use of the term, prostaglandin or "PG" will mean the optically active form of that prostaglandin thereby referred to with the same absolute configuration as PGF$_2\alpha$, obtained from mammalian tissues.

The term "prostaglandin-type" (PG-type) product, as used herein, refers to any cyclopentane derivative herein which is useful for at least one of the same pharmacological purposes as the prostaglandins.

The formulas, as drawn herein, which depict a prostaglandin-type product or an intermediate useful in preparing a prostaglandin-type compounds, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type products.

The term "prostaglandin analog," as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type product herein, the term prostaglandin analog refers to the compound of that formula or a mixture comprising that compound and the enantiomer thereof.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

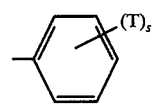

wherein T is alkyl of one to 3 carbon atoms, inclusive, fluoro, chloro, trifluoromethyl, or alkoxy of one to 3 carbon atoms, inclusive; and $s$ is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

Amides within the scope of amido groups of the formula $-NR_{21}R_{22}$ are the unsubstituted amide ($-NH_2$), methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Still further examples are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Still further examples are benzylamide, 2-phenylethylamide, 2-phenylethylamide, N-methyl-N-benzylamide, and dibenzylamide. Still further examples are anilide, p-chloroanilide, m-chloroanilide, 2,4,4-dichloroanilide, 2,4,6-trichloroanilide, p-methylanilide, m-methylanilide, p-ethylanilide, t-butylanilide, p-carboxyanilide, and p-methoxycarbonylanilide.

Amides within the scope of the cycloamido groups described above are pyrrolidylamide, piperidylamide, morpholinylamide, hexamethyleneiminylamide, piperazinylamide, pyrrolinylamide, and 3,4-didehydropiperidinylamide.

Amides within the scope of carbonylamido of the formula $-NR_{23}COR_{21}$ are methylcarbonylamide, ethylcarbonylamide, phenylcarbonylamide, and benzylcarbonylamide. Admies within the scope of sulfonylamido of the formula $-NR_{23}SO_2R_{21}$ are methylsulfonylamide, ethylsulfonylamide, phenylsulfonylamide, p-tolylsulfonylamide, and benzylsulfonylamide.

Substituted phenol esters within the scope of the p-substituted phenoxy groups described above are p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Within the scope of the novel PG-type compounds described above, certain of these compounds are preferred in that they exhibit increased potency, duration or selectivity of action, provide more easily stabilized pharmacological formulations, or exhibit a decreased toxicity at the appropriate therapeutic or prophylactic dose. Accordingly, the preferred compounds herein include those compounds wherein $g$ is 3 or 1, most especially 1, are preferred.

In cases where increased pharmacological potency is desired, those compounds wherein the C-15 hydroxy is of the "alpha" configuration are especially preferred. With regard to the various substituents at C-15 and C-16, it is preferred that at least one of $R_3$, $R_4$, and $R_5$ be hydrogen. Further, in the event one of $R_3$ and $R_4$ is methyl or fluoro, it is preferred that $R_3$ and $R_4$ both be methyl or fluoro, respectively.

For those compounds herein where $Y_1$ is $-C\equiv C-$, those compounds wherein $R_3$, $R_4$, and $R_5$ are all hydrogen are preferred.

For the $\omega$-aryl (i.e., where $R_7$ is aryl) compounds herein, preferred compounds are those wherein $s$ is zero or one and T is chloro, fluoro or trifluoromethyl.

Regarding the nature of the C-2 substitution for the novel carboxyamides disclosed herein, the preferred amido substituents are those wherein $R_{21}$ and $R_{22}$ are preferably hydrogen or alkyl of 1 to 8 carbon atoms, inclusive, being the same or different, preferably with the total number of carbon atoms in $R_{21}$ and $R_{22}$ being less than or equal to 8. More especially preferred are those carboxyamide substituents wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to four.

For convenience in preparation and use, the amido group $-NH_2$ is most especially preferred.

With regard to the various cycloamido groups described above, preferred cycloamido groups are those wherein the $R_{21}$ and $R_{22}$ substituents represent the preferred values therefor as described for the acyclic amido groups above. Most preferably, $R_{21}$ and $R_{22}$ are both hydrogen.

With regard to the carbonylamido groups described above, $R_{23}$ is preferably hydrogen and $R_{21}$ is preferably alkyl of one to 8 carbon atoms, inclusive. More preferably, $R_{21}$ is alkyl of one to 4 carbon atoms, inclusive, especially being methyl. Finally, with regard to the sulfonylamido groups described above, $R_{21}$ and $R_{23}$ most preferably exhibit those preferred values as described for carbonylamido groups.

With the exception of the 16-phenyl-9-methylene-9-deoxy-PGF-type compounds described herein, the various 9-deoxy-9-methylene-PGF-type acids and corresponding esters are prepared as described in U.S. Ser. No. 682,848.

The 16-phenyl-9-deoxy-9-methylene-PG-type acids and C-1 esters, alcohols and amines herein are prepared as described in Ser. No. 682,848, now U.S. Pat. No. 4,060,534, except that the C-12 side chain is prepared employing a phosphonate of the formula

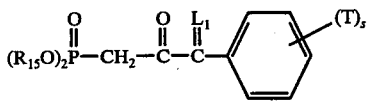

wherein $L_1$, T, and s are as defined above and $R_{15}$ is alkyl of one to 8 carbon atoms, inclusive.

These phosphonates are known in the art or readily prepared by methods known in the art. For example, they may be prepared from the appropriate aromatic acid ester by condensation with the anion of dimethyl methylphosphonate generated from reaction of this compound with n-butyllithium. Accordingly, lower alkyl esters of acids of the formula

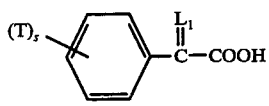

are employed. These acids, e.g., phenylacetic acid, are known in the art or prepared by methods known in the art.

For example, the propionic and 2-methylpropionic acids described above are prepared by α-methylation or α,α-dimethylation of the corresponding acetic acid. Alkylation proceeds by conventional methods, for example, treatment with methyl iodide. Thus, by this method, the aromatic acetic acid is first reacted with an equivalent amount of lithium diisopropylamide and thereafter reacted with the methyl iodide methylating agent. When monomethylation is required, a single equivalent of methyl iodide is employed. For dimethylation, an excess (greater than two equivalents) of base and methylating agent is employed. The reaction conveniently proceeds at ambient temperature in a suitable organic solvent, e.g., tetrahydrofuran.

For the preparation of α-fluoro and α,α-difluorophenylacetic acids (including the corresponding substituted phenyl acids), fluorination proceeds first by reaction of the phenyl- or substituted phenyl acetic acids with lithium diisopropylamide, as described above, and thereafter by reaction with the fluorinating agent, perchlorylfluoride ($ClO_3F$). Conveniently, perchlorylfluoride gas is reacted with the aromatic acetic acid-lithium diisopropylamide complex at low temperature. In preparation of the monofluoroacetic acids, reaction conditions are maintained until one equivalent of the perchlorofluoride is consumed. This reaction proceeds conveniently in numerous organic solvents, including tetrahydrofuran.

With regard to the preparation of the p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the 9-deoxy-9-methylene-PGF-type carboxylic acids, the corresponding carboxyamides are prepared by one of several amidation methods known in the prior art. See, for example, U.S. Pat. No. 3,981,868, issued Sept. 21, 1976 for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the 9-deoxy-9-methylene-PGF-type acids are prepared is, first, by transformation of such free acids to corresponding mixed acid anhydrides. By this procedure, the prostaglandin-type free acid is first neutralized with an equivalent of an amine base, and thereafter reacted a slight stoichiometric excess of a chloroformate corresponding to the mixed anhydride to be prepared.

The amine base preferred for neutralization is triethylamine, although other amines (e.g. pyridine, methyldiethylamine) are likewise employed. Further, a convenient, readily available chloroformate for use in the mixed anhydride production is isobutyl chloroformate.

The mixed anhydride formation proceeds by conventional methods and accordingly the 9-deoxy-9-methylene-PGF-type free acid is mixed with both the tertiary amine base and the chloroformate in a suitable solvent (e.g. aqueous tetrahydrofuran), allowing the reaction to proceed at −10° to 20° C.

Thereafter, the mixed anhydride is converted to the corresponding amido or cycloamido derivative by reaction with the amine corresponding to the amide to be prepared. In the case where the simple amide (—$NH_2$) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g. methylamine).

Thereafter, the novel 9-deoxy-9-methylene-PGF-type amido or cycloamido derivative is recovered from the reaction mixture by conventional techniques.

The carbonylamido and sulfonylamido derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl of sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PG-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

As indicated above, the novel 16-phenyl-9-deoxy-9-methylene-PGF-type compounds as well as the novel prostaglandin carboxyamides and p-substituted phenyl esters of the present disclosure, especially the preferred compounds described herein, correspond to the previously known 9-deoxy-9-methylene-PGF-type acids and esters, in that these novel prostaglandin 16-phenyl-PGF-type compounds, carboxyamides and esters exhibit the same prostaglandin-type biological responses as for the known acids and esters. Specifically, the present 16-phenyl-PGF-type compounds, carboxyamides and p-substituted phenyl esters are useful for each of the known purposes for which the corresponding known acids and esters are used, and, moreover, are used in the same manner as such known acids and esters.

The previously known 9-deoxy-9-methylene-PGF-type acids and esters are all potent in causing numerous biological responses at low dosages. Furthermore, these free acids and esters, while exhibiting substantial biological activity by numerous routes of administration, provide orally induced prostaglandin-type responses for inconveniently short durations, or caused undesirable side effects when orally administered at therapeutic doses.

In striking contrast, however, the novel prostaglandin carboxyamides of the present invention are substantially more useful with regard to orally induced biological responses, exhibiting a surprising and unexpected prolongation of prostaglandin-type activity by this method of administration, while concomitantly reducing the incidence of undesirable side effects. Moreover, this prolongation of oral activity is particularly and especially pronounced in the employment of the prostaglandin-type carboxamides of the present disclosure as regulators of procreation and fertility, in all mammalian species (being menstrual or estrus cycle regulators, labor inducers and abortafacients) and antiasthma and antithrombotic agents.

Accordingly, the novel prostaglandin carboxyamides are useful whenever medical therapy requires a pharmacological agent to inhibit platelet aggregation, reduce the adhesive character of platelet or remove or prevent the formation of thrombi in mammals, including man, rabbits, and rats. For example, these compounds are useful in the treatment and prevention of myocardial infractions, post-operative thrombosis, and the maintenance of patency of vascular grafts following surgery. Moreover, these novel prostaglandin-type carboxyamides are useful to treat conditions such as atherosclerosis, arteriosclerosis, blood clotting defects due to lipemia and other clinical conditions in which the underlying etiology is associates with lipid imbalance or hyperlipidemia. For the purposes described above, the present prostaglandin-type carboxyamides are administered systemically, e.g., intravenously, subcutaneously, intramuscularly in the form of sterile implants for prolonged action. However, the surprising and unexpectedly prolonged oral activity of these compounds renders oral administration the preferred systemic route of administration.

The carboxyamides described herein are thus useful in the treatment of asthma, being, for example, bronchodilators or inhibitors of mediators (such as SRS-A, and histamine) which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, but preferably, orally in the form of tablets, capsules, or liquids by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these compounds are optionally combined with other anti-asthmatic agents, such as sympathomimetics (isoproterenol, phenylepihrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

Further, the carboxyamides herein are useful in place of oxytocin to induce labor are used in pregnant female animals including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral, being the preferred route for these compounds.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered orably at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Finally, these compounds are further useful in domestic animals as an abortifacient (especially for feedlot heifers), as an aid to estrous detection, or for regulation or synchronization of estrous. Domestic animals indicated for such treatment include horses, cattle, sheep, and swine. The regulation or synchronization of estrous allows for more efficient management of both conception and labor by enabling a herdsman to breed all his femals in short pre-defined intervals, thus facilitating, for example, artificial insemination. This synchronization results in a higher percentage of live births than the percentage achieved by natural control. The compound is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrous at the same time.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine," herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

Preparation 1 — 16-Phenyl-17,18,19,20-tetranor-PGE$_2$ and its bis(tetrahydropyranyl ether).

A. A 57% sodium hydride dispersion in mineral oil (6.56 g. of sodium hydride) in 500 ml. of tetrahydrofuran is cooled to 0° C. and treated dropwise over 30 min. with a solution of dimethyl 2-oxo-3-phenylpropylphosphonate in 80 ml. of tetrahydrofuran. This mixture is then stirred at 25° C. for one hour and thereafter cooled to 0° C. The cooled solution is then treated with 42.7 g. of 3α-benzoyloxy-5α-hydroxy-2β-carboxaldehyde-1α-cyclopentaneacetic acid γ-lactone in 300 ml. of tetrahydrofuran, added dropwise. This mixture is then stirred to 25° C. for 3 hrs. and treated with 15 ml. of acetic acid. After rotary evaporation of the tetrahydrofuran solvent, the residue is diluted with water and extracted with methylene chloride. The extract is then washed with brine, dried over magnesium sulfate, and concentrated under reduced pressure. Crude product is then crystallized from ethyl acetate, yielding 33.7 g. of 3α-benzoyloxy-5α-hydroxy-2β-(3-oxo-4-phenyl-trans-1-butenyl)-1α-cyclopentaneacetic acid γ-lactone. Melting point is 126° to 128° C.

B. To a stirred suspension of 60.5 g. of zinc chloride in 350 ml. of 1,2-dimethoxyethane, maintained at ambient temperature, is added 16.7 g. of sodium borohydride. This mixture is then stirred at 25° C. for 18 hrs. and cooled to 0° C. The cooled solution is then treated with 43.7 g. of the reaction product of part A, above, in 350 ml. of dimethoxyethane. This reaction is then allowed to warm to ambient temperature and stirred for an additional hour. After cooling again to 0° C. the reaction mixture is then treated with 200 ml. of 1 molar aqueous sodium bisulfate, added dropwise with stirring. The stirred mixture is then poured into ice and brine and thereafter extracted with ethyl acetate. The ethyl acetate extracts are then washed with brine and aqueous sodium bicarbonate and thereafter dried over sodium sulfate. Evaporation under reduced pressure yields crude 3α-benzoyloxy-5α-hydroxy-2β-[(3RS)-3-hydroxy-4-phenyl-trans-1-butenyl]-1α-cyclopentane acetic acid γ-lactone. Chromatographing on 3.1 kg. of silica gel packed with 40% ethyl acetate in hexane yields pure 3S and 3R isomers.

C. To a stirred solution of 20 g. of the (3R)-3-hydroxy isomer of part B above in 230 ml. of methanol is added 7.1 g. of potassium carbonate. The resulting mixture is then stirred for one hour at ambient temperature and the methanol thereafter distilled under reduced pressure. The resulting residue is then diluted with ice water and acidified with dilute potassium disulfate. Ethyl acetate extracts are then washed with water and brine, dried over sodium sulfate, and evaporated to yield crude 3α,5α-dihydroxy-2β-(3α-hydroxy-4-phenyl-trans-1-butenyl)-1α-cyclopentaneacetic acid γ-lactone. Chromatographing with 80–100% ethyl acetate in Skellysolve B yields pure lactone diol.

D. A solution of 12.7 g. of the reaction product of part C above and 310 ml. of methylene chloride is treated with 930 mg. of pyridine hydrochloride and 68 ml. of freshly distilled dihydropyran. The resulting solution is then stirred under a nitrogen atmosphere at ambient temperature for 18 hrs. The reaction mixture is then diluted with 400 ml. of ethyl acetate, cooled to 0° C., and treated with 100 ml. of aqueous sodium bicarbonate. The aqueous and organic layers are then separated and the organic layer washed with brine, dried over sodium sulfate, and evaporated under reduced pressure. 3α,5α-Dihydroxy-2β-(3α-hydroxy-4-phenyl-trans-1-butenyl)-1α-cyclopentaneacetic acid γ-lactone bis(tetrahydropyranyl ether), 18.59 g. is obtained as a colorless oil. This material is then used without further purification in part E.

E. A solution of 18.5 g. of the reaction product of part D in 200 ml. of toluene is cooled to −78° C. under a nitrogen atmosphere. Dropwise treatment over 30 min. with 155 ml. of a 0.56 molar solution of diisobutylaluminum hydride and toluene is followed by stirring at −78° C. for an additional 30 min. The resulting mixture is then treated with 45 ml. of water and 70 ml. of tetrahydrofuran, added dropwise. The reaction mixture is then diluted with an additional 300 ml. of toluene and allowed to warm to ambient temperature. Stirring is continued for 2 hrs. at 25° C. The mixture is then filtered through diatomaceous earth. The solids are then washed with benzene and ethyl acetate and the combined filtrate washed with brine, dried over magnesium silfate, and concentrated under reduced pressure to yield crude 3α,5α-dihydroxy-2β-(3α-hydroxy-4-phenyl-trans-1-butenyl)-1α-cyclopentaneacid acetaldehyde γ-lactol, bis(tetrahydropyranyl ether). Silica gel TLC $R_f$ is 0.55 in ethyl acetate.

F. A 50% sodium hydride dispersion in mineral oil (11.63 g. of sodium hydride) in 400 ml. of anhydrous dimethyl sulfoxide is stirred at 60°-65° C. under nitrogen for 90 min. The resulting solution is then cooled to 15°-20° C. and treated with 53.7 g. of 4-carboxybutyltriphenylphosphonium bromide. The resulting solution is then stirred at ambient temperature for 45 min. and then cooled to 15° C. and treated with 18 g. of the reaction product of part F in 200 ml. of dimethyl sulfoxide. This mixture is then stirred for 2 hrs. at 25° C. and then poured into a mixture of 500 ml. of aqueous ammonium chloride, ice, water, 500 ml. and diethyl ether (800 ml.). Diethyl ether extracts (3-500 ml. extracts) are washed with brine, dried over sodium sulfate and concentrated under reduced pressure. The product thusly obtained is chromatographed on 2 kg. of acid-washed silica gel packed with 20% ethyl acetate and hexane. Eluting with 40-60% ethyl acetate in hexane yields 18.59 g. of pure 16-phenyl-17,18,19,20-tetranor-PGF$_2$α, 11,15-bis(tetrahydropyranyl ether).

G. A solution of 2 g. of the reaction product of part F above and 50 ml. of acetone is cooled to −20° C. and treated dropwise with 1.5 ml. of Jones reagent. After 10 min. at −20° C. 1 ml. of isopropanol is added and the mixture stirred for 15 min. at −20° C. The resulting mixture is then diluted with 500 ml. of cold water and extracted with methylene chloride. The extracts are washed with water and brine, dried over sodium sulfate and concentrated under reduced pressure, yielding 16-phenyl-17,18,19,20-tetranor-PGE$_2$, bis(tetrahydropyranyl ether).

The tetrahydropyranyl ether described in the preceding paragraph may be hydrolyzed to the corresponding diol as follows:

16-phenyl-17,18,19,20-tetranor-PGE$_2$, bis(tetrahydropyranyl ether), prepared above, is dissolved in 9 ml. of tetrahydrofuran and diluted with 16 ml. of acetic acid and 30 ml. of water. Stirring for 2 hrs. at 40° C. under nitrogen is followed by dilution with 300 ml. of water. The diluted mixture is then lyophilized and the residue chromatographed on 300 g. of acid-washed silica gel packed with 60% ethyl acetate and hexane. Eluting with 60-80% ethyl acetate in hexane yields 300 ml. of pure 16-phenyl-17,18,19,20-tetranor-PGE$_2$, which when recrystallized from ethyl acetate hexane yields 207 mg. of product. Melting point is 88° to 89° C., infrared absorption observed at 3480, 3000, 1735, 1715, 1605, 1495, 1265, 1255, 1190, 1095, 990, and 705 cm$^{-1}$. The mass spectrum exhibits peaks at 354, 336, 318, and 281.

EXAMPLE 1

9-Deoxy-9-methylene-16-phenyl-17,18,19,20-tetranor-PGF$_2$, methyl ester (Formula I: $X_1$ is —COOCH$_3$, $Z_1$ is cis—CH═CH—(CH$_2$)$_3$—, $Y_1$ is trans—CH═CH—, $R_3$, $R_4$, and $R_5$ are all hydrogen, the hydroxy of the $M_1$ moiety is in the alpha configuration, and s is zero) and its corresponding free acid.

A. 16-phenyl-17,18,19,20-tetranor-PGE$_2$, bis(tetrahydropyranyl ether), prepared in Preparation 1, part G, in 100 ml. of acetonitrile is treated with 12 ml. of methyl iodide and 6 ml. of N,N-diisopropylethylamine. The resulting mixture is then stirred for 4 hours at ambient temperature and the reaction mixture poured into ice and brine and extracted with ethyl acetate. The combined extracts are then washed with water, diluted sodium bisulfate, aqueous sodium bicarbonate, and brine. Drying over magnesium sulfate and concentrating under reduced pressure yields crude 16-phenyl-17,18,19,20-tetranor-PGE$_2$, methyl ester, — bis(tetrahydropyranyl ether).

B. To a sitrred solution at 0° C. of 2.0 g. of methylphenyl-N-methylsulfoximine in 45 ml. of tetrahydrofuran is added 4 ml. of 2.94 M methylmagnesiumchloride (in tetrahydrofuran). Addition proceeds over 5-10 min. and after an additional 15 min. at 0° C., the resulting sulfoximine solution is cooled to −78° C. and added to a solution, also at −78° C., of 4.1 g. of the reaction product of part A in 25 ml. of tetrahydrofuran. After addition over 10 min., the reaction mixture is stirred for 3 hrs. at −78° C. Thereafter an additional portion of sulfoximine anion is prepared, as described above, and added to the reaction mixture until thin layer chromatographic analysis indicates the reaction to be complete. Thereafter the reaction mixture is poured into 160 ml. of saturated ammonium chloride and ice and extracted with diethyl ether. The diethyl ether extracts are then washed with brine, dried over sodium sulfate, and concentrated under reduced pressure to yield a crude product.

The crude product of the preceding paragraph is then dissolved in 250 ml. of tetrahydrofuran, 40 ml. of water, and 40 ml. of acetic acid. This mixture is then treated with the aluminum amalgam prepared as described in part C. The resulting gray suspension is then stirred for 1.5 hrs. in a 15°-20° C. water bath, and filtered through a pad of diatomaceous earth. The filter cake is then washed with tetrahydrofuran and the combined filtrate is then concentrated under reduced pressure. The residue thusly obtained is diluted with brine and extracted with 40% ethyl acetate and hexane. The extracts are then washed with brine, sodium phosphate, and brine. Drying over sodium sulfate and concentrating under reduced pressure yields crude 9-deoxy-9-methylene-16-phenoxy-17,18,19,20-tetranor-PGF$_2$, methyl ester, bis(tetrahydropyranyl ether).

C. The aluminum amalgam employed in part B is prepared from 8.7 g. of 20-mesh aluminum metal, washed with two 40 ml. aliquots of diethyl ether and two 40 ml. aliquots of methanol. Thereafter the washed aluminum metal is treated with 8.7 g. of mercuric chloride in 400 ml. of water. This suspension is then agitated for about 45 seconds and decanted. The resulting amalgam is then washed successively with methanol and diethyl ether and employed immediately.

D. The crude reaction product from part B is then dissolved in 15 ml. of tetrahydrofuran, diluted with 30 ml. of water and 75 ml. of acetic acid, and stirred at 40° C. for 2.5 hrs. The resulting mixture is then poured into brine and extracted with ethyl acetate. The ethyl acetate extracts are then washed with dilute sodium phosphate and brine and dried over sodium sulfate. Concentration under reduced pressure yields 4.0 g. of crude title product. The crude title product is then chromatographed on 400 g. of silica gel packed with 20% ethyl acetate and hexane. Elution with 40-70% ethyl acetate in hexane yields 1.01 g. of pure 9-deoxy-9-methylene-16-phenoxy-17,18,19,20-tetranor-PGF$_2$, methyl ester. Infrared absorptions are observed at 3550, 3050, 1745, 1660, 1440, 1080, 1030, 970, 885, 750, and 700 cm$^{-1}$. NMR absorptions are observed at 7.22, 5.70-5.20, 5.0-4.8, 4.5-4.0, 3.85 — 3.45, and 3.15 δ. The mass spectrum of the trimethylsilyl derivative exhibits a high resolution peak at 513.2856 (the demethylated molecular ion) and other peaks at 528 (the molecular ion), 497, 437, 407, 347, 257, and 91.

E. A solution of the reaction product of part D (the methyl ester), 908 mg., in 20 ml. of methanol is treated with 10 ml. of aqueous 2 N sodium hydroxide. The resulting solution is stirred for 4.5 hrs. at 25° C. and the reaction mixture is then cooled to 0° C. Dilution with icewater, acidification with dilute sodium bisulfate and extraction with ethyl acetate yields crude 9-deoxy-9-methylene-16-phenoxy-17,18,19,20-tetranor-PGF$_2$.
Thus crude product is then chromatographed on 200 g. of acid-washed silica gel packed with 30% acetone and hexane. Elution with 40% acetone and hexane yields 829 g. of pure title free acid. Infrared absorptions are observed at 3400, 1720, 1660, 1240, 1050, 975, 890, 750 and 700 cm$^{-1}$. NMR absorptions are observed at 735–7.10, 5.65–5.10, 5.0–4.75, and 4.45–3.45 $\delta$. The mass spectrum of the trimethylsilyl derivative exhibits a molecular ion at 585 and a high resolution peak at 571.3095 (the demethylated molecular ion), and other peaks at 495, 481, 405, 315, 243, and 91.

Following the procedure described in Preparation 1 and Example 1, as well as the procedures described in United States Serial No. 682,848, the various other 16-phenyl-9-deoxy-9-methylene-PGF-type compounds described herein are prepared.

EXAMPLE 2

9-Deoxy-9-methylene-16,16-dimethyl-PGF$_2$, p-hydroxybenzaldehyde semicarbazone ester (Formula II: L$_4$ is

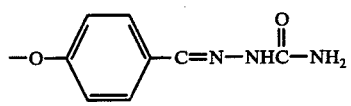

Z$_1$ is cis—CH=CH—(CH$_2$)$_3$—, Y$_1$ is trans—CH=CH—, R$_5$ is hydrogen and the hydroxy of the M$_1$ moiety is in the alpha configuration, R$_3$ and R$_4$ are both methyl, and R$_7$ is n-butyl).

A solution of 1.0 g. of 9-deoxy-9-methylene-16,16-dimethyl-PGF$_2$ in 45 ml. of dry acetone is cooled to 0° C. and treated dropwise with 0.51 ml. of triethylamine. Thereafter 0.48 ml. of isobutylchloroformate is added. This mixture is stirred for 10 min. after which a triethylamine hydrochloride precipitate forms. A solution of 1.32 g. of p-hydroxybenzaldehyde semicarbazone in 13 ml. of pyridine is then added and the mixture allowed to warm to 25° C. This mixture is then stirred for 60 min. and thereafter concentrated under reduced pressure. The residue is then dissolved in ethyl acetate and filtered. The filter cake is then washed with ethyl acetate and the combined filtrate is evaporated and chromatographed on 200 g. of silica gel packed with 5% isopropanol and hexane. Eluting with 10% isopropanol and hexane yields pure product which is then rechromatographed with tetrahydrofuran. Thereupon 1.29 g. of pure title product is obtained. Crystallization from ethyl acetate and hexane yields 700 mg. of crystalline product. Melting point is 85°–87° C. Infrared absorptions are observed at 3700, 3400, 1750, 1690, 1610, 1570, 1420, 1200, 1160, 1130, 1085, 974 cm$^{-1}$.

EXAMPLE 3

9-Deoxy-9-methylene-16,16-dimethyl-PGF$_2$, amide (Formula I: L$_4$ is —NH$_2$, and Z$_1$, Y$_1$, M$_1$, L$_1$ and R$_7$ are as defined in Example 2).

A solution of 393 mg. of 9-deoxy-9-methylene-16,16-dimethyl-PGF$_2$ and 5 ml. of acetone is treated with 0.14 ml. of triethylamine. This mixture is then cooled under a nitrogen atmosphere to $-10°$ C. and treated with 0.13 ml. of isobutylchloroformate. To this mixture is then added after 10 min. at $-10°$ C. 5 ml. of acetonitrile saturated with ammonia. The resulting mixture is then warmed to 25° C. and stirred for 15 min. Following the removal of solvents under reduced pressure, the residue is diluted with brine and extracted with ethyl acetate. The ethyl acetate extracts are then washed with aqueous sodium bicarbonate and brine, dried over magnesium sulfate, and evaporated under reduced pressure to yield 400 mg. of crude title product. This crude product is then chromatographed on 75 g. of acid-washed silica gel packed with ethyl acetate. Eluting with ethyl acetate yields 154 mg. of pure title product. Additionally, 220 mg. of approximately 90% pure title product is obtained. Infrared absorptions are observed at 3400, 1675, 1620, 1080, 1020, 1000, 970 and 885 cm$^{-1}$. NMR absorptions are observed at 6.05, 5.7–5.2, 4.90, 3.9–3.3, 0.87, and 0.82 $\delta$. Mass spectrum of the trimethylsilyl derivative exhibits a high resolution molecular ion at 593.4074 and other peaks at 578, 536, 494, 404, and 243.

EXAMPLE 4

9-Deoxy-9-methylene-16,16-dimethyl-PGF$_2$, p-carboxyanilide (Formula II: L$_4$ is

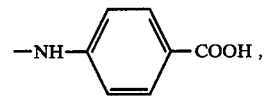

Z$_1$, Y$_1$, M$_1$, L$_1$, and R$_7$ are as defined in Example 2).

To a solution of 393 mg. of 9-deoxy-9-methylene-16,16-dimethyl-PGF$_2$ at $-10°$ C. in 5 ml. of acetone is added 0.14 ml. of triethylamine, followed by addition of 0.13 ml. of isobutylchloroformate. The resulting mixture is then stirred at $-10°$ C. for 10 min. and thereafter treated with a mixture of 250 mg. of p-aminobenzoic acid, 0.2 ml. of triethylamine, and 5 ml. of acetone. The resulting mixture is then warmed to 25° C. and stirred for 20 min. Thereafter the stirred mixture is poured into cold dilute aqueous sodium bisulfate and extracted with ethyl acetate. The organic extracts are then washed with brine, dried over magnesium sulfate and evaporated to yield 626 mg. of crude product. This crude product is then chromatographed on 75 g. of silica gel packed with 40% ethyl acetate in hexane. Eluting with 40 to 70% ethyl acetate in hexane yields 502 mg. of pure title product. Trituration of this material with diethyl ether $-78°$ C. yields a solid, which after filtration and drying, weighs 120 mg. Melting is observed at 60-85° C. Infrared absorptions are observed at 3400, 3300, 1680, 1600, 1530, 1400, 1370, 1250, 1175, 970, 860 and 775 cm$^{-1}$. NMR absorptions are observed at 8.1–7.55, 5.7–5.25, 5.00–4.75, 3.90–3.50, 0.85 and 0.81 $\delta$. The mass spectrum of the trimethylsilyl derivative exhibits a molecular ion at 713, a demethylated molecular ion at 698, a high resolution peak at 614.3167, (a deheptylated molecular ion) and other peaks at 524, 495, 404, and 314.

EXAMPLE 5

9-Deoxy-9-methylene-16,16-dimethyl-PGF$_2$, methylsulphonylamide (Formula II: L$_4$ is —NHSO$_2$CH$_3$, Z$_1$, Y$_1$, M$_1$, L$_1$, and R$_7$ are as defined in Example 2).

To a stirred solution of 480 mg. of 9-deoxy-9-methylene-16,16-dimethyl-PGF$_2$ in 6.0 ml. of dimethylformamide and 0.142 g. of triethylamine is added with stirring followed by addition of 0.19 g. of isobutyl chloroformate. This mixture is then stirred at 0° C. for 25 min. at which time 0.685 g. of methylsulfonamide sodium salt (prepared by adding 1.33 ml. of 4.4 N methanolic sodium methoxide to a solution of 0.604 g. of methanesulfonamide in 2.0 ml. of methanol, concentrating the mixture under reduced pressure, adding benzene to the residue, and again concentrating the mixture under reduced pressure). Thereafter 1.25 ml. of hexamethylphosphoramide is added and the mixture stirred at ambient temperature for 16 hrs. Acidification with cold dilute hydrochloric acid is followed by extraction with ethyl acetate. The organic extract is then washed with water, brine and dried over magnesium sulfate. Concentration at reduced pressure yields a residue (0.76 g.) which is chromatographed on a 100 g. column of silica gel packed with 10% methanol in methylene chloride. Eluting with 7.5% methanol in methylene chloride yields crude product (contaminated with dimethylformamide) which is then diluted with ether, washed with cold dilute hydrochloric acid, water, and saturated brine. Drying over magnesium sulfate and concentrating under reduced pressure yields a residue of 0.57 g. of pure title product. Silica gel TLC R$_f$ is 0.46 in 7.5% methanol in methylene chloride. NMR absorptions are observed at 5.42–5.65, 4.78–4.98, 3.72–3.88, 3.36 and 3.26 δ.

Following the procedure of Example 2, but employing the respective p-substituted phenols corresponding to the various p-substituted phenyl esters described above, there are prepared the various 9-deoxy-9-methylene-16,16-dimethyl-PG$_2$, p-substituted phenyl esters described herein. Further, employing each of the various 9-deoxy-9-methylene-PG$_2$ compounds described herein or described in U.S. Pat. No. 4,060,534, in place of 9-deoxy-9-methylene-16,16-dimethyl-PGF$_2$, and employing each of the various p-substituted phenols described above, there are prepared each of the various 9-deoxy-9-methylene-PGF-type, p-substituted phenyl esters described herein.

Following the procedure of Example 3, but employing amines corresponding to each of the various amido and cycloamido groups described above in place of ammonia, there are prepared the various amido and cycloamido derivatives of 9-deoxy-9-methylene-16,16-dimethyl-PGF$_2$ described herein. Further, employing each of the various 9-deoxy-9-methylene-PGF$_2$ compounds described above or described in U.S. Pat. No. 4,060,534 and each of the various amines described above, there are prepared each of the various 9-deoxy-9-methylene-PGF$_2$ amido and cycloamido derivatives disclosed herein.

In particular, following the procedure of the Examples provided above, but employing as starting material the various 9-deoxy-9-methylene-PGF-type free acids described in U.S. Pat. No. 4,060,534 as above, there are prepared 9-deoxy-9-methylene-PGF amido, cycloamido, sulphonylamido, or carbonylamido derivatives or p-substituted phenyl esters which exhibit the following side chain variations:

16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
16-Methyl-16-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;

17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
2,2-Difluoro-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,18,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(-p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,-14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,-19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-18,19,20-trinor-13,14-dihydro-;

2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
3,7-Inter-m-phenylene-3-oxa-4,5,6-trinor-;
3,7-Inter-m-phenylene-3-oxa-4,5,6-trinor-16-methyl-;
3,7-Inter-m-phenylene-3-oxa-4,5,6-trinor-16,16-dimethyl-;
3,7-Inter-m-phenylene-3-oxa-4,5,6-trinor-16-fluoro-;
3,7-Inter-m-phenylene-3-oxa-4,5,6-trinor-16,16-difluoro-;
3,7-Inter-m-phenylene-3-oxa-17-phenyl-4,5,6,18,19,20-hexanor-;
3,7-Inter-m-phenylene-3-oxa-17-(m-trifluoromethylphenyl)-4,5,6,18,19,20-hexanor-;
3,7-Inter-m-phenylene-3-oxa-17-(m-chlorophenyl)-4,5,6,18,19,20-hexanor-;
3,7-Inter-m-phenylene-3-oxa-17-(p-fluorophenyl)-4,5,6,18,19,20-hexanor-;
3,7-Inter-m-phenylene-3-oxa-16-methyl-17-phenyl-4,5,6,18,19,20-hexanor-;
3,7-Inter-m-phenylene-3-oxa-16,16-dimethyl-17-phenyl-4,5,6,18,19,20-hexanor-;
3,7-Inter-m-phenylene-3-oxa-16-fluoro-17-phenyl-4,5,6,18,19,20-hexanor-;
3,7-Inter-m-phenylene-3-oxa-16,16-difluoro-17-phenyl-4,5,6,18,19,20-hexanor-;
3,7-Inter-m-phenylene-3-oxa-16-phenyl-4,5,6,17,18,19,-20-heptanor-;
3,7-Inter-m-phenylene-3-oxa-16-(m-trifluoromethylphenyl)-4,5,6,17,18,19,20-heptanor-;
3,7-Inter-m-phenylene-3-oxa-16-(m-chlorophenyl)-4,5,6,17,18,19,20-heptanor-;
3,7-Inter-m-phenylene-3-oxa-4,5,6-trinor-16-(p-fluorophenyl)-4,5,6,17,18,19,20-heptanor-;
3,7-Inter-m-phenylene-3-oxa-16-phenyl-4,5,6,18,19,20-hexanor-;
3,7-Inter-m-phenylene-3-oxa-4,5,6-trinor-16-methyl-16-phenyl-4,5,6,18,19,20-hexanor-;
3,7-Inter-m-phenylene-3-oxa-16-phenoxy-4,5,6,17,18,19,-20-heptanor-;
3,7-Inter-m-phenylene-3-oxa-16-(m-trifluoromethylphenoxy)-4,5,6,17,18,19,20-heptanor-;
3,7-Inter-m-phenylene-3-oxa-16-(m-chlorophenoxy)-4,5,6,17,18,19,20-heptanor-;
3,7-Inter-m-phenylene-3-oxa-4,5,6-trinor-16-(p-fluorophenoxy)-4,5,6,17,18,19,20-heptanor-;
3,7-Inter-m-phenylene-3-oxa-16-phenoxy-4,5,6,18,19,20-hexanor-;
3,7-Inter-m-phenylene-3-oxa-4,5,6-trinor-16-methyl-16-phenoxy-4,5,6,18,19,20-hexanor-;
3,7-Inter-m-phenylene-3-oxa-4,5,6-trinor-13,14-didehydro-;
3,7-Inter-m-phenylene-3-oxa-4,5,6-trinor-16-methyl-13,14-didehydro-;
3,7-Inter-m-phenylene-3-oxa-4,5,6-trinor-16,16-dimethyl-13,14-didehydro-;
3,7-Inter-m-phenylene-3-oxa-4,5,6-trinor-16-fluoro-13,14-didehydro-;
3,7-Inter-m-phenylene-3-oxa-4,5,6-trinor-16,16-difluoro-13,14-didehydro-;
3,7-Inter-m-phenylene-3-oxa-17-phenyl-4,5,6,18,19,20-hexanor-13,14-didehydro-;
3,7-Inter-m-phenylene-3-oxa-17-(m-trifluoromethylphenyl)-4,5,6,18,19,20-hexanor-13,14-didehydro-;
3,7-Inter-m-phenylene-3-oxa-17-(m-chlorophenyl)-4,5,6,18,19,20-hexanor-13,14-didehydro-;
3,7-Inter-m-phenylene-3-oxa-17-(p-fluorophenyl)-4,5,6,18,19,20-hexanor-13,14-didehydro-;
3,7-Inter-m-phenylene-3-oxa-16-methyl-17-phenyl-4,5,6,18,19,20-hexanor-13,14-didehydro-;
3,7-Inter-m-phenylene-3-oxa-16,16-dimethyl-17-phenyl-4,5,6,18,19,20-hexanor-13,14-didehydro-;
3,7-Inter-m-phenylene-3-oxa-16-fluoro-17-phenyl-4,5,6,18,19,20-hexanor-13,14-didehydro-;
3,7-Inter-m-phenylene-3-oxa-16,16-difluoro-17-phenyl-4,5,6,18,19,20-hexanor-13,14-didehydro-;
3,7-Inter-m-phenylene-3-oxa-16-phenyl-4,5,6,17,18,19,-20-heptanor-13,14-didehydro-;
3,7-Inter-m-phenylene-3-oxa-16-(m-trifluoromethylphenyl)-4,5,6,17,18,19,20-heptanor-13,14-didehydro-;
3,7-Inter-m-phenylene-3-oxa-16-(m-chlorophenyl)-4,5,6,17,18,19,20-heptanor-13,14-didehydro-;
3,7-Inter-m-phenylene-3-oxa-16-phenyl-4,5,6,18,19,20-hexanor-13,14-didehydro-;
3,7-Inter-m-phenylene-3-oxa-16-methyl-16-phenyl-4,5,6,18,19,20-hexanor-13,14-didehydro-;
3,7-Inter-m-phenylene-3-oxa-16-phenoxy-4,5,6,17,18,-19,20-heptanor-13,14-didehydro-;
3,7-Inter-m-phenylene-3-oxa-16-(m-trifluoromethylphenoxy)-4,5,6,17,18,19,20-heptanor-13,14-didehydro-;
3,7-Inter-m-phenylene-3-oxa-16-(m-chlorophenoxy)-4,5,6,17,18,19,20-heptanor-13,14-didehydro-;
3,7-Inter-m-phenylene-3-oxa-16-phenoxy-4,5,6,18,19,20-hexanor-13,14-didehydro-;
3,7-Inter-m-phenylene-3-oxa-16-methyl-16-phenoxy-4,5,6,18,19,20-hexanor-13,14-didehydro-;
3,7-Inter-m-phenylene-3-oxa-4,5,6-trinor-13,14-dihydro-;
3,7-Inter-m-phenylene-3-oxa-4,5,6-trinor-13,14-dihydro-;
3,7-Inter-m-phenylene-3-oxa-4,5,6-trinor-16-methyl-13,14-dihydro-;
3,7-Inter-m-phenylene-3-oxa-4,5,6-trinor-16,16-dimethyl-13,14-dihydro-;
3,7-Inter-m-phenylene-3-oxa-4,5,6-trinor-16-fluoro-13,14-dihydro-;
3,7-Inter-m-phenylene-3-oxa-4,5,6-trinor-16,16-difluoro-13,14-dihydro-;
3,7-Inter-m-phenylene-3-oxa-17-phenyl-4,5,6,18,19,20-trinor-13,14-dihydro-;
3,7-Inter-m-phenylene-3-oxa-17-(m-trifluoromethylphenyl)-4,5,6,18,19,20-hexanor-13,14-dihydro-;
3,7-Inter-m-phenylene-3-oxa-17-(m-chlorophenyl)-4,5,6,18,19,20-hexanor-13,14-dihydro-;
3,7-Inter-m-phenylene-3-oxa-17-(p-fluorophenyl)-4,5,6,18,19,20-hexanor-13,14-dihydro-;
3,7-Inter-m-phenylene-3-oxa-16-methyl-17-phenyl-4,5,6,18,19,20-hexanor-13,14-dihydro-;
3,7-Inter-m-phenylene-3-oxa-16,16-dimethyl-17-phenyl-4,5,6,18,19,20-hexanor-13,14-dihydro-;
3,7-Inter-m-phenylene-3-oxa-16-fluoro-17-phenyl-4,5,6,18,19,20-hexanor-13,14-dihydro-;

3,7-Inter-m-phenylene-3-oxa-16,16-difluoro-17-phenyl-4,5,6,18,19,20-hexanor-13,14-dihydro-;
3,7-Inter-m-phenylene-3-oxa-16-phenyl-4,5,6,17,18,19,20-heptanor-13,14-dihydro-;
3,7-Inter-m-phenylene-3-oxa-16-(m-trifluoromethylphenyl)-4,5,6,17,18,19,20-heptanor-13,14-dihydro-;
3,7-Inter-m-phenylene-3-oxa-16-(m-chlorophenyl)-4,5,6,17,18,19,20-heptanor-13,14-dihydro-;
3,7-Inter-m-phenylene-3-oxa-16-(p-fluorophenyl)-4,5,6,17,18,19,20-heptanor-13,14-dihydro-;
3,7-Inter-m-phenylene-3-oxa-16-phenyl-4,5,6,18,19,20-hexanor-13,14-dihydro-;
3,7-Inter-m-phenylene-3-oxa-16-methyl-16-phenyl-4,5,6,18,19,20-hexanor-13,14-dihydro-;
3,7-Inter-m-phenylene-3-oxa-16-phenoxy-4,5,6,17,18,19,-20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18,19,20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-phenoxy-4,5,6,18,19,20-hexanor-13,14-dihydro-;
3,7-Inter-m-phenylene-3-oxa-16-methyl-16-phenoxy-4,5,6,18,19,20-hexanor-13,14-dihydro-;
3,7-Inter-m-phenylene-4,5,6-trinor-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,-19,20-hexanor-;
3,7-Inter-m-phenylene-17-(p-fluorophenyl)-4,5,6,18,19,-20-hexanor-;
3,7-Inter-m-phenylene-16-methyl-17-phenyl-4,5,6,18,-19,20-hexanor-;
3,7-Inter-m-phenylene-16,16-dimethyl-17-phenyl-4,5,6-18,19,20-hexanor-;
3,7-Inter-m-phenylene-16-fluoro-17-phenyl-4,5,6-18,19,20-hexanor-;
3,7-Inter-m-phenylene-16,16-difluoro-17-phenyl-4,5,6-18,19,20-hexanor-;
3,7-Inter-m-phenylene-16-phenyl-17-phenyl-4,5,6,17,-18,19,20-heptanor-;
3,7-Inter-m-phenylene-16-(m-trifluoromethylphenyl)-4,5,6,17,18,19,20-heptanor-;
3,7-Inter-m-phenylene-16-(m-chlorophenyl)-4,5,6,17,-18,19,20-heptanor-;
3,7-Inter-m-phenylene-16-(p-fluorophenyl)-4,5,6,17,-18,19,20-heptanor-;
3,7-Inter-m-phenylene-16-phenyl-4,5,6,18,19,20-hexanor-;
3,7-Inter-m-phenylene-16-methyl-16-phenyl-4,5,6,-18,19,20-hexanor-;
3,7-Inter-m-phenylene-16-phenoxy-17-phenyl-4,5,6,-17,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,-17,18,19,20-heptanor-;
3,7-Inter-m-phenylene-16-(p-fluorophenoxy)-4,5,6,-17,18,19,20-heptanor-;
3,7-Inter-m-phenylene-16-phenoxy-4,5,6,18,19,20-hexanor-;
3,7-Inter-m-phenylene-16-methyl-16-phenoxy-4,5,6,-18,19,20-hexanor-;
3,7-Inter-m-phenylene-4,5,6-trinor-13,14-didehydro-;
3,7-Inter-m-phenylene-4,5,6-trinor-16-methyl-13,14-didehydro-;
3,7-Inter-m-phenylene-4,5,6-trinor-16,16-dimethyl-13,14-didehydro-;
3,7-Inter-m-phenylene-4,5,6-trinor-16-fluoro-13,14-didehydro-;
3,7-Inter-m-phenylene-4,5,6-trinor-16,16-difluoro-13,14-didehydro-;
3,7-Inter-m-phenylene-17-phenyl-4,5,6,18,19,20-hexanor-13,14-didehydro-;
3,7-Inter-m-phenylene-17-(m-trifluoromethylphenyl)-4,5,6,18,19,20-hexanor-13,14-didehydro-;
3,7-Inter-m-phenylene-17-(m-chlorophenyl)-4,5,6,-18,19,20-hexanor-13,14-didehydro-;
3,7-Inter-m-phenylene-17-(p-fluorophenyl)-4,5,6,-18,19,20-hexanor-13,14-didehydro-;
3,7-Inter-m-phenylene-16-methyl-17-phenyl-4,5,6,-18,19,20-hexanor-13,14-didehydro-;
3,7-Inter-m-phenylene-16,16-dimethyl-17-phenyl-4,5,6,18,19,20-hexanor-13,14-didehydro-;
3,7-Inter-m-phenylene-16-fluoro-17-phenyl-4,5,6,-18,19,20-hexanor-13,14-didehydro-;
3,7-Inter-m-phenylene-16,16-difluoro-17-phenyl-4,5,6,-18,19,20-hexanor-13,14-didehydro-;
3,7-Inter-m-phenylene-16-phenyl-4,5,6,17,18,19,20-heptanor-13,14-didehydro-;
3,7-Inter-m-phenylene-16-(m-trifluoromethylphenyl)-4,5,6,17,18,19,20-heptanor-13,14-didehydro-;
3,7-Inter-m-phenylene-16-(m-chlorophenyl)-4,5,6,-17,18,19,20-heptanor-13,14-didehydro-;
3,7-Inter-m-phenylene-16-phenoxy-4,5,6,18,19,20-hexanor-13,14-didehydro-;
3,7-Inter-m-phenylene-16-methyl-16-phenoxy-4,5,6,-18,19,20-hexanor-13,14-didehydro-;
3,7-Inter-m-phenylene-16-phenoxy-4,5,6,17,18,19,20-heptanor-13,14-didehydro-;
3,7-Inter-m-phenylene-16-(m-trifluoromethylphenoxy)-4,5,6,17,18,19,20-heptanor-13,14-didehydro-;
3,7-Inter-m-phenylene-16-(m-chlorophenoxy)-4,5,6,-17,18,19,20-heptanor-13,14-didehydro-;
3,7-Inter-m-phenylene-16-phenoxy-4,5,6,18,19,20-hexanor-13,14-didehydro-;
3,7-Inter-m-phenylene-16-methyl-16-phenoxy-4,5,6,-18,19,20-hexanor-13,14-didehydro-;
3,7-Inter-m-phenylene-4,5,6-trinor-13,14-didehydro-;
3,7-Inter-m-phenylene-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-phenylene-17-(m-trifluoromethylphenyl)-4,5,6,18,19,20-hexanor-13,14-dihydro-;
3,7-Inter-m-phenylene-17-(m-chlorophenyl)-4,5,6,18,-19,20-hexanor-13,14-dihydro-;
3,7-Inter-m-phenylene-17-(p-fluorophenyl)-4,5,6,18,-19,20-hexanor-13,14-dihydro-;

3,7-Inter-m-phenylene-16-methyl-17-phenyl-4,5,6,-18,19,20-hexanor-13,14-dihydro-;
3,7-Inter-m-phenylene-16,16-dimethyl-17-phenyl-4,5,6,18,19,20-hexanor-13,14-dihydro-;
3,7-Inter-m-phenylene-16-fluoro-17-phenyl-4,5,6,18,19,20-hexanor-13,14-dihydro-;
3,7-Inter-m-phenylene-16,16-difluoro-17-phenyl-4,5,6,18,19,20-hexanor-13,14-dihydro-;
3,7-Inter-m-phenylene-16-phenyl-4,5,6,17,18,19,20-heptanor-13,14-dihydro-;
3,7-Inter-m-phenylene-16-(m-trifluoromethylphenyl)-4,5,6,17,18,19,20-heptanor-13,14-dihydro-;
3,7-Inter-m-phenylene-16-(m-chlorophenyl)-4,5,6,-17,18,19,20-heptanor-13,14-dihydro-;
3,7-Inter-m-phenylene-16-(p-fluorophenyl)-4,5,6,-17,18,19,20-heptanor-13,14-dihydro-;
3,7-Inter-m-phenylene-16-phenyl-4,5,6,18,19,20-hexanor-13,14-dihydro-;
3,7-Inter-m-phenylene-16-methyl-16-phenyl-4,5,6,-18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,-17,18,19,20-heptanor-13,14-dihydro-;
3,7-Inter-m-phenylene-16-(p-fluorophenoxy)-4,5,6,-17,18,19,20-heptanor-13,14-dihydro-;
3,7-Inter-m-phenylene-16-phenoxy-4,5,6,18,19,20-hexanor-13,14-dihydro-;
3,7-Inter-m-phenylene-16-methyl-16-phenoxy-4,5,6-18,19,20-hexanor-13,14-dihydro-;
5-Oxa-;
5-Oxa-16-methyl-;
5-Oxa-16,16-dimethyl-;
5-Oxa-16-fluoro-;
5-Oxa-16,16-difluoro-;
5-Oxa-17-phenyl-18,19,20-trinor-;
5-Oxa-17-(m-trifluoromethylphenyl)-18,19,20-trinor-;
5-Oxa-17-(m-chlorophenyl)-18,19,20-trinor-;
5-Oxa-17-(p-fluorophenyl)-18,19,20-trinor-;
5-Oxa-16-methyl-17-phenyl-18,19,20-trinor-;
5-Oxa-16,16-dimethyl-17-phenyl-18,19,20-trinor-;
5-Oxa-16-fluoro-17-phenyl-18,19,20-trinor-;
5-Oxa-16,16-difluoro-17-phenyl-18,19,20-trinor-;
5-Oxa-16-phenyl-17,18,19,20,-tetranor-;
5-Oxa-16-(m-trifluoromethylphenyl)-17,18,19,20-tetranor-;
5-Oxa-16-(m-chlorophenyl)-17,18,19,20-tetranor-;
5-Oxa-16-(p-fluorophenyl)-17,18,19,20-tetranor-;
5-Oxa-16-phenyl-18,19,20-trinor-;
5-Oxa-16-methyl-16-phenyl-18,19,20-trinor-;
5-Oxa-16-phenoxy-17,18,19,20-tetranor-;
5-Oxa-16-(m-trifluoromethylphenoxy)-17,18,19,20-tetranor-;
5-Oxa-16-(m-chlorophenoxy)-17,18,19,20-tetranor-;
5-Oxa-16-(p-fluorophenoxy)-17,18,19,20-tetranor-;
5-Oxa-16-phenoxy-18,19,20-trinor-;
5-Oxa-16-methyl-16-phenoxy-18,19,20-trinor-;
5-Oxa-13,14-didehydro-;
5-Oxa-16-methyl-13,14-didehydro-;
5-Oxa-16,16-dimethyl-13,14-didehydro-;
5-Oxa-16-fluoro-13,14-didehydro-;
5-Oxa-16,16-difluoro-13,14-didehydro-;
5-Oxa-17-phenyl-18,19,20-trinor-13,14-didehydro-;
5-Oxa-17-(m-trifluoromethylphenyl)-18,19,20-trinor-13,14-didehydro-;
5-Oxa-17-(m-chlorophenyl)-18,19,20-trinor-13,14-didehydro-;
5-Oxa-17-(p-fluorophenyl)-18,19,20-trinor-13,14-didehydro-;
5-Oxa-16-methyl-17-phenyl-18,19,20-trinor-13,14-didehydro-;
5-Oxa-16,16-dimethyl-17-phenyl-18,19,20-trinor-13,14-didehydro-;
5-Oxa-16-fluoro-17-phenyl-18,19,20-trinor-13,14-didehydro-;
5-Oxa-16,16-difluoro-17-phenyl-18,19,20-trinor-13,14-didehydro-;
5-Oxa-16-phenyl-17,18,19,20-tetranor-13,14-didehydro-;
5-Oxa-16-(m-trifluoromethylphenyl)-17,18,19,20-tetranor-13,14-didehydro-;
5-Oxa-16-(m-chlorophenyl)-17,18,19,20-tetranor-13,14-didehydro-;
5-Oxa-16-phenyl-18,19,20-trinor-13,14-didehydro-;
5-Oxa-16-methyl-16-phenyl-18,19,20-trinor-13,14-didehydro-;
5-Oxa-16-phenoxy-17,18,19,20-tetranor-13,14-didehydro-;
5-Oxa-16-(m-trifluoromethylphenoxy)-17,18,19,20-tetranor-13,14-didehydro-;
5-Oxa-16-(m-chlorophenoxy)-17,18,19,20-tetranor-13,14-didehydro-;
5-Oxa-16-phenoxy-18,19,20-trinor-13,14-didehydro-;
5-Oxa-16-methyl-16-phenoxy-18,19,20-trinor-13,14-didehydro-;
5-Oxa-13,14-dihydro-;
5-Oxa-16-methyl-13,14-dihydro-;
5-Oxa-16,16-dimethyl-13,14-dihydro-;
5-Oxa-16-fluoro-13,14-dihydro-;
5-Oxa-16,16-difluoro-13,14-dihydro-;
5-Oxa-17-phenyl-18,19,20-trinor-13,14-dihydro-;
5-Oxa-17-(m-trifluoromethylphenyl)-18,19,20-trinor-13,14-dihydro-;
5-Oxa-17-(m-chlorophenyl)-18,19,20-trinor-13,14-dihydro-;
5-Oxa-17-(p-fluorophenyl)-18,19,20-trinor-13,14-dihydro-;
5-Oxa-16-methyl-17-phenyl-18,19,20-trinor-13,14-dihydro-;
5-Oxa-16,16-Dimethyl-17-phenyl-18,19,20-trinor-13,14-dihydro-;
5-Oxa-16-fluoro-17-phenyl-18,19,20-trinor-13,14-dihydro-;
5-Oxa-16,16-difluoro-17-phenyl-18,19,20-trinor-13,14-dihydro-;
5-Oxa-16-phenyl-17,18,19,20-tetranor-13,14-dihydro-;
5-Oxa-16-(m-trifluoromethylphenyl)-17,18,19,20-tetranor-13,14-dihydro-;
5-Oxa-16-(m-chlorophenyl)-17,18,19,20-tetranor-13,14-dihydro-;
5-Oxa-16-(p-fluorophenyl)-17,18,19,20-tetranor-13,14-dihydro-;
5-Oxa-16-phenyl-18,19,20-trinor-13,14-dihydro-;
5-Oxa-16-methyl-16-phenyl-18,19,20-trinor-13,14-dihydro-;
5-Oxa-16-phenoxy-17,18,19,20-tetranor-13,14-dihydro-;
5-Oxa-16-(m-trifluoromethylphenoxy)-17,18,19,20-tetranor-13,14-dihydro-;
5-Oxa-16-(m-chlorophenoxy)-17,18,19,20-tetranor-13,14-dihydro-;

5-Oxa-16-(p-fluorophenoxy)-17,18,19,20-tetranor-13,14-dihydro-;
5-Oxa-16-phenoxy-18,19,20-trinor-13,14-dihydro-;
5-Oxa-16-methyl-16-phenoxy-18,19,20-trinor-13,14-dihydro-;

I claim:
1. A prostaglandin analog of the formula

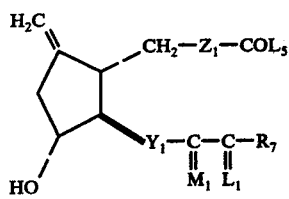

wherein $Y_1$ is trans—CH=CH—, —C≡C—, or —CH$_2$CH$_2$—;
wherein $M_1$ is

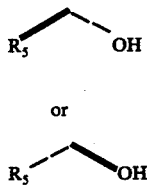

or

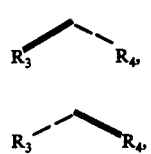

wherein $R_5$ is hydrogen or methyl;
wherein $L_1$ is

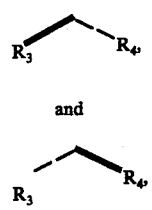

or a mixture of

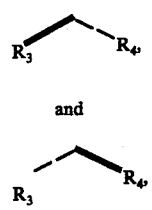

and wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

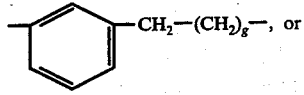

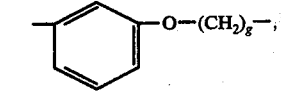

wherein g is one, 2, or 3;
wherein $R_7$ is
(1) —(CH$_2$)$_m$—CH$_3$,

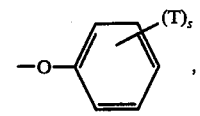

or

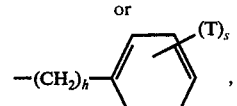

wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

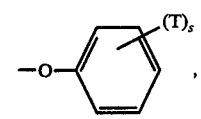

wherein T and s are as defined above, only when $R_3$ and $R_4$ are hydrogen or methyl, being the same or different; and
wherein $L_5$ is
(1) amido of the formula —NR$_{21}$R$_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive; or
(2) carbonylamido of the formula —NR$_{23}$COR$_{21}$, wherein $R_{23}$ is hydrogen or alkyl of one to 4 carbon atoms and $R_{21}$ is as defined above.

2. A prostaglandin analog according to claim 1, wherein $Y_1$ is —C≡C—.
3. 9-Deoxy-9-methylene-13,14-didehydro-PGF$_2$, amide, a prostaglandin analog according to claim 62.
4. A prostaglandin analog according to claim 1, wherein $Y_1$ is —CH$_2$CH$_2$—.
5. 9-Deoxy-9-methylene-13,14-dihydro-PGF$_2$, amide, a prostaglandin analog according to claim 4.
6. A prostaglandin analog according to claim 1, wherein $Y_1$ is trans—CH=CH—.
7. A prostaglandin analog according to claim 6, wherein $Z_1$ is aromatic.

8. 9-Deoxy-9-methylene-3,7-inter-m-phenylene-3-oxa-4,5,6-trinor-PGF$_1$, amide, a prostaglandin analog according to claim 7.

9. 9-Deoxy-9-methylene-3,7-inter-m-phenylene-4,5,6-trinor-PGF$_1$, amide, a prostaglandin analog according to claim 7.

10. A prostaglandin analog according to claim 6, wherein $Z_1$ is aliphatic.

11. A prostaglandin analog according to claim 10, wherein $M_1$ is

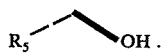

12. 15-epi-9-deoxy-9-methylene-PGF$_2$, amide, a prostaglandin analog according to claim 4.

13. A prostaglandin analog according to claim 10, wherein $M_1$ is

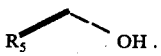

14. A prostaglandin analog according to claim 13, wherein $Z_1$ is cis—CH=CH—CH$_2$—(CH$_2$)$_g$—CH$_2$—.

15. A prostaglandin analog according to claim 14, wherein $R_7$ is

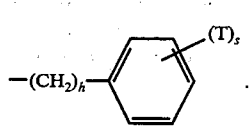

16. 9-Deoxy-9-methylene-17-phenyl-18,19,20,-trinor-PGF$_2$, amide, a prostaglandin analog according to claim 15.

17. A prostaglandin analog according to claim 14, wherein $R_7$ is

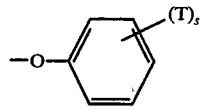

18. 9-Deoxy-9-methylene-16-phenoxy-17,18,19,20-tetranor-PGF$_1$, amide, a prostaglandin analog according to claim 17.

19. A prostaglandin analog according to claim 14, wherein $R_7$ is —(CH$_2$)$_m$—CH$_3$.

20. A prostaglandin analog according to claim 19, wherein $m$ is 3.

21. A prostaglandin analog according to claim 20, wherein $L_5$ is carbonylamido of the formula —NR$_{23}$COR$_{21}$.

22. 9-Deoxy-9-methylene-16,16-dimethyl-trinor-PGF$_2$, methylcarbonylamide, a prostaglandin analog according to claim 21.

23. A prostaglandin analog according to claim 20, wherein $L_5$ is amido of the formula —NR$_{21}$R$_{22}$.

24. A prostaglandin analog according to claim 23, wherein $g$ is 3.

25. 2a,2b-Dihomo-9-deoxy-9-methylene-15-methyl-PGF$_2$, amide, a prostaglandin analog according to claim 24.

26. A prostaglandin analog according to claim 23, wherein $g$ is one.

27. A prostaglandin analog according to claim 26, wherein at least one of $R_3$ and $R_4$ is methyl.

28. 9-Deoxy-9-methylene-16,16-dimethyl-PGF$_2$, amide, a prostaglandin analog according to claim 27.

29. A prostaglandin analog according to claim 26, wherein at least one of $R_3$ and $R_4$ is fluoro.

30. 9-Deoxy-9-methylene-16,16-difluoro-PGF$_2$, amide, a prostaglandin analog according to claim 29.

31. A prostaglandin analog according to claim 26, wherein $R_3$ and $R_4$ are both hydrogen.

32. A prostaglandin analog according to claim 31, wherein $R_5$ is methyl.

33. 9-Deoxy-9-methylene-15-methyl-PGF$_2$, amide, a prostaglandin analog according to claim 32.

34. A prostaglandin analog accorrding to claim 31, wherein $R_5$ is hydrogen.

35. 9-Deoxy-9-methylene-PGF$_1$, n-propylamide, a prostaglandin analog according to claim 34.

36. 9-Deoxy-9-methylene-PGF$_1$, ethylamide, a prostaglandin analog according to claim 34.

37. 9-Deoxy-9-methylene-PGF$_1$, methylamide, a prostaglandin analog according to claim 34.

38. 9-Deoxy-9-methylene-PGF$_1$, amide, a prostaglandin analog according to claim 34.

* * * * *

UNITED STATES PATENT OFFICE
CERTIFICATE OF CORRECTION

Patent No. 4,098,805  Dated 4 July 1978

Inventor(s) Gordon L. Bundy

It is certified that error appears in the above-identified patent and that said Letters Patent are hereby corrected as shown below:

Column 12, line 45, "administered orably" should read -- administered orally --;
Column 14, line 68, "silfate," should read -- sulfate, --;
Column 31, line 18, "according to claim 4" should read -- according to claim 11 --.

Signed and Sealed this

Twenty-fourth Day of November 1981

[SEAL]

Attest:

GERALD J. MOSSINGHOFF

Attesting Officer    Commissioner of Patents and Trademarks